United States Patent [19] [11] 4,115,205
Murtha [45] Sep. 19, 1978

[54] SEPARATION OF PHENOL-, CYCLOHEXANONE-, AND CYCLOHEXYLBENZENE-CONTAINING MIXTURES EMPLOYING AN N-SUBSTITUTED LACTAM

[75] Inventor: Timothy P. Murtha, Bartlesville, Okla.

[73] Assignee: Phillips Petroleum Company, Bartlesville, Okla.

[21] Appl. No.: 817,768

[22] Filed: Jul. 21, 1977

[51] Int. Cl.² .................. B01D 3/40; C07C 39/04; C07C 45/24
[52] U.S. Cl. .................. 203/60; 203/84; 260/586 R; 568/757
[58] Field of Search .......... 203/60, 58, 57, 51, 203/38, 84; 260/586 P, 621 A, 621 P, 586 R

[56] References Cited
U.S. PATENT DOCUMENTS

| | | | |
|---|---|---|---|
| 2,762,760 | 9/1956 | Walker | 260/621 |
| 3,210,259 | 10/1965 | Cornell et al. | 203/58 |
| 4,016,049 | 4/1977 | Fozzard et al. | 260/621 A |
| 4,019,965 | 4/1977 | Fozzard | 260/621 C |
| 4,021,490 | 5/1977 | Hudson | 260/621 C |

Primary Examiner—Wilbur L. Bascomb, Jr.

[57] ABSTRACT

Phenol-, cyclohexanone-, and cyclohexylbenzene-containing mixtures are extractively distilled employing an N-substituted lactam to provide overhead a high purity cyclohexanone and a kettle product containing phenol, cyclohexylbenzene when it is present in the mixture treated, and the N-substituted lactam.

4 Claims, 1 Drawing Figure

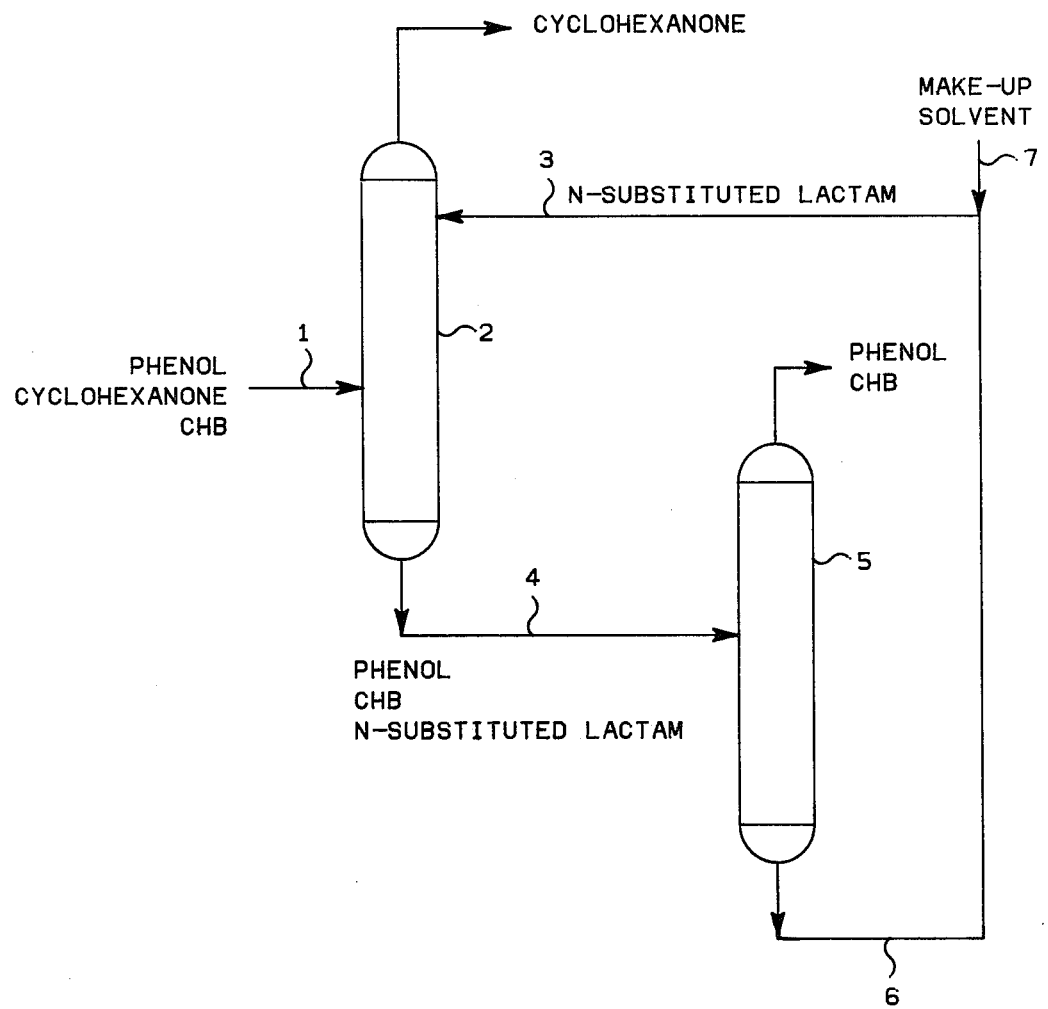

SEPARATION OF PHENOL-, CYCLOHEXANONE-, AND CYCLOHEXYLBENZENE-CONTAINING MIXTURES EMPLOYING AN N-SUBSTITUTED LACTAM

This invention relates to separation of phenol from its azeotropes, including phenol-cyclohexanone azeotrope, which may be in the presence of cyclohexylbenzene. In one of its aspects, the invention relates to the recovery of phenol and cyclohexanone from the cleavage products resulting from cleavage of the oxidation product of cyclohexylbenzene to provide cyclohexylbenzene hydroperoxide which then is converted to produce the phenol, cyclohexanone, and any unreacted cyclohexylbenzene.

In one of its concepts, the invention provides a process for extractive distillation of a mixture containing phenol and cyclohexanone employing as an agent an N-substituted lactam. In another of its concepts, the invention provides a process for obtaining high purity cyclohexanone from mixtures resulting from the oxidation of cyclohexylbenzene to provide cyclohexylbenzene hydroperoxide.

In a further concept of the invention, the extractive distillation yields an overhead product consisting essentially of high purity cyclohexanone.

Cyclohexylbenzene (CHB) can be converted to phenol and cyclohexanone via cyclohexylbenzene hydroperoxide. The acid catalyzed cleavage of cyclohexylbenzene hydroperoxide in the presence of unoxidized CHB results in a mixture of CHB, phenol, and cyclohexanone. This mixture is difficult to separate by conventional distillation techniques because phenol and cyclohexanone form an azeotrope (b.p. 184° C. at atmospheric pressure) containing about 72 weight percent phenol. In addition, CHB codistills with this azeotrope.

It is an object of this invention to separate mixtures containing phenol and cyclohexanone which also can contain cyclohexylbenzene. It is another object of this invention to provide an extractive distillation agent or solvent to separate mixtures as described herein. It is a still further object of the invention to provide an extractive distillation operation comprising a mixture of one or more agents or solvents also described here.

Other aspects, concepts, objects, and the several advantages of this invention are apparent from a study of this disclosure and the appended claims.

According to the present invention, a mixture containing phenol and cyclohexanone, which may contain cyclohexylbenzene, is extractively distilled employing an N-substituted lactam, and, thus separated, to produce as an overhead product a fraction containing essentially high purity cyclohexanone.

Mixture to be Separated

Any mixture of phenol, cyclohexanone, and CHB or mixture of phenol and cyclohexanone can be used. It is within the scope of this invention to remove by suitable methods a portion of any of the components from the mixture to be separated prior to the extractive distillation with the N-substituted lactam. For example, any excess of cyclohexanone over the quantity present in the azeotrope can be first distilled from the mixture as an essentially pure material. Since CHB codistills with the phenol/cyclohexanone azeotrope in quantities of about 2 to 10 weight percent, any excess of CHB over that amount can be removed by fractional distillation to take the phenol/cyclohexanone mixture containing about 2 to 10 weight percent CHB overhead. It is also within the scope of this invention to remove essentially all of the CHB from the mixture by suitable techniques, such as extractive distillation, prior to the extractive distillation of this invention.

SOLVENT

The N-substituted lactam solvent to be used in the extractive distillation of this invention can contain up to 30 carbon atoms and can be represented by the general formula:

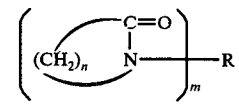

wherein R is selected from a group consisting of alkyl radicals containing 2 to 20 carbon atoms, cycloalkyl radicals containing 5 to 20 carbon atoms, alkylene radicals containing 2 to 20 carbon atoms, aryl or substituted aryl radicals containing 6 to 18 carbon atoms with the substituent groups being one or more or a mixture of alkyl, alkoxy, cycloalkyl, halogen, or the like, arylene radicals containing 6 to 18 carbon atoms, aralkyl radicals containing 7 to 18 carbon atoms and wherein $n$ is an integer from 3 to 8 and $m$ is 1 or 2 and wherein the selected solvent has a boiling point above the boiling point of phenol (182° C. at atmospheric pressure) to facilitate the separation of the solvent for recycling by fractional distillation. However, low levels of phenol (up to about 10 weight percent phenol) can be present in the recovered and recycled solvent with no detrimental effect on the extractive distillation. For ease of handling, it is generally preferred that the N-substituted lactams used as an extractive distillation solvent to be a liquid or low melting (below about 80° C.) solid.

Specific examples of N-substituted lactams suitable for the extractive distillation of this invention include N-ethyl-2-pyrrolidone, N-butyl-2-pyrrolidone, N-hexadecyl-2-pyrrolidone, N-cyclohexyl-2-pyrrolidone, N-phenyl-2-pyrrolidone, N-(p-methoxyphenyl)-2-pyrrolidone, N-benzyl-2-pyrrolidone, p-phenylene-N,N'-bis(2-pyrrolidone), hexamethylene-N,N'-bis(2-pyrrolidone), N-ethyl-2-piperidone, and the like. These compounds are either commercially available or can be prepared by known reactions. For example, the reaction of cyclohexylamine with γ-butyrolactone yields N-cyclohexyl-2-pyrrolidone.

Extractive Distillation Conditions

The extractive distillation of this invention can be carried out under a variety of conditions. The volume ratio of N-substituted lactam to feedstream will be broadly from 0.1/1 to 10/1, preferably 1/1 to 5/1. To avoid possible thermal decomposition or other reactions during the extractive distillation, head temperatures below 135° C., preferably below 100° C., are used with a reduced pressure sufficient to allow the separation to occur.

Referring to the diagram which further illustrates the process of this invention, a feed mixture consisting essentially of phenol, cyclohexanone, and CHB is passed by 1 to an extractive distillation column 2. The N-substituted lactam solvent or mixture of solvents of this invention is introduced into the extractive distillation column 2 by 3 at a point above the point of introduction of the feed mixture.

A vaporous overhead steam consisting essentially of cyclohexanone is withdrawn from the extractive distillation column 2. A liquid bottom stream consisting essentially of phenol, CHB, and N-substituted lactam is withdrawn from the extractive distillation column 2 by 4 and passed to distillation column 5.

In the distillation column 5, the phenol/CHB/N-substituted lactam mixture is separated into a vaporous overhead stream consisting essentially of phenol and CHB and a liquid bottoms stream consisting essentially of N-substituted lactam which is passed by 6 and 3 to the extractive distillation column 2. Makeup N-substituted lactam is added by 7 if necessary. The phenol-CHB overhead stream can be passed to another separation stage to separate this mixture.

When the mixture to be separated consists essentially of phenol and cyclohexanone, the bottom stream from extractive distillation column 2 will consist essentially of phenol and N-substituted lactam and the overhead stream from distillation column 5 will consist essentially of phenol.

EXAMPLES

In the following examples, extractive distillations were conducted in an electrically heated 0.75" (19 mm) × 36" (914 mm) column containing 0.25" (6.4 mm) Por-Pak stainless steel perforated screen packing. The solvent was fed through a rotameter and heating section to an introduction port 3" (76 mm) from the top of the column. The mixture to be separated was fed through a rotameter and heating section to an introduction port 18" (457 mm) from the top of the column. The overhead and kettle products were collected and then analyzed by gas-liquid phase chromatography (glpc) on a Hewlett Packard 5710A chromatograph equipped with a flame ionization detector.

Fractional distillations were conducted with an electrically heated 0.75" (19 mm) × 24" (610 mm) column containing #3008 stainless steel Heli-Pak [0.092" (2.34 mm) × 0.175" (4.44 mm) × 0.175" (4.44 mm)] packing. The overhead products were collected and then analyzed by glpc.

The mixtures to be separated were prepared from commercial, reagent grade phenol and cyclohexanone and cyclohexylbenzene (98% purity) prepared by the reductive alkylation of benzene.

EXAMPLE I

Two runs (Runs 1 and 2) were carried out according to the instant invention utilizing N-cyclohexyl-2-pyrrolidone as the solvent for the extractive distillation of a mixture containing 68 weight percent phenol, 27 weight percent cyclohexanone, and 5 weight percent CHB.

The extractive distillation conditions in Run 1 were 120 mm Hg pressure, 55°–78° C. head temperature, and a 2.6/1 solvent/feed volume ratio. Over a six-hour run time, the overhead fractions contained cyclohexanone with an average purity of 99.5 weight percent. The cyclohexanone collected was 94 weight percent of the amount of cyclohexanone fed to the column during the run.

Run 2 was conducted like Run 1 except the head temperature was 73°–76° C. and the solvent/feed volume ratio was decreased to 2.4/1. Over a 6.5-hour run time, the overhead fractions contained cyclohexanone with an average purity of 99.5 weight percent. The cyclohexanone collected was 97.3 weight percent of the amount fed to the column during the run.

The bottoms products from Runs 1 and 2 were combined and fractionally distilled at 80 mm Hg pressure to give earlier overhead fractions containing primarily phenol and CHB and later overhead fractions containing mixtures of N-cyclohexyl-2-pyrrolidone and phenol. Example II shows that a mixture of N-cyclohexyl-2-pyrrolidone and phenol (in a 95:5 weight ratio) is suitable from the extractive distillation of this invention.

The results of these runs demonstrate operability of the instant invention utilizing N-cyclohexyl-2-pyrrolidone as solvent for the separation of cyclohexanone in high yield and high purity from a mixture of phenol, cyclohexanone, and CHB and for the recovery of N-cyclohexyl-2-pyrrolidone containing some phenol for recycle.

EXAMPLE II

Run 3 was conducted according to the instant invention utilizing a mixture of 95 weight percent N-cyclohexyl-2-pyrrolidone and 5 weight percent phenol as solvent for the extractive distillation of a mixture containing 68 weight percent phenol, 27 weight percent cyclohexanone, and 5 weight percent CHB. The extractive distillation conditions were 80 mm Hg pressure, 67°–74° C. head temperature (with a brief period of overheating to 90° C.), and 3.1/1 solvent/feed volume rartio. Over a 6.5-hour run time, the overhead fractions contained cyclohexanone with an average purity of 99.5 weight percent. The cyclohexanone collected was 91.5 weight percent of the amount fed to the column during the run. It is believed that the determined amount of cyclohexanone collected is low due to a brief solvent flow stoppage and resulting overheating during the run. An analysis of two earlier fractions showed a recovery of 100 weight percent of the cyclohexanone with a purity of 99.1 weight percent.

The kettle product was fractionally distilled at 80 mm Hg pressure to separate phenol and CHB overhead with only traces of the solvent. Later fractions were mixtures of N-cyclohexyl-2-pyrrolidone and phenol.

The results of this run show that a 95:5 weight ratio mixture of N-cyclohexyl-2-pyrrolidone and phenol successfully separates cyclohexanone in high yield and high purity from a mixture of phenol, cyclohexanone, and CHB, and the solvent mixture can be recoverd for recycle.

EXAMPLE III

Run 4 was conducted according to the instant invention utilizing hexamethylene-N,N'-bis(2-pyrrolidone) as solvent for the extractive distillation of a mixture containing 68 weight percent phenol, 27 weight percent cyclohexanone, and 5 weight percent CHB. The extractive distillation conditions were 120 mm Hg pressure, 86°–90° C. head temperature, and a 2.7/1 solvent/feed volume ratio. Over a 6-hour run time, the overhead fractions contained cyclohexanone with an average purity of 98.2 weight percent. The cyclohexanone collected was 100 weight percent of the amount fed to the column during the run.

The kettle product from this extractive distillation was fractionally distilled to give a very clean separation of phenol and CHB from the hexamethylene-N,N'-bis(2-pyrrolidone).

The results of this run show that hexamethylene-N,N'-bis(2-pyrrolidone) successfully separates cyclohexanone in high yield and high purity from a mixture of phenol, cyclohexanone, and CHB, and that the solvent can be recovered by fractional distillation for recycle.

EXAMPLE IV

A control run (Run 5) was conducted utilizing N-methyl-2-pyrrolidone, a solvent outside the scope of this invention, as solvent for the extractive distillation of a mixture containing 68 weight percent phenol, 27 weight percent cyclohexanone, and 5 weight percent CHB. The extractive distillation conditions were 120 mm Hg pressure, 80°–84° C. head temperarture, and a 3.1/1 solvent/feed volume ratio. Over a 6-hour run time, the overhead fractions contained cyclohexanone with an average purity of 99.4 weight percent. The cyclohexanone collected was 100 weight percent of the amount fed to the column during the run. The kettle product from the extractive distillation was fractionally distilled at 80 mm Hg pressure. The solvent could not be cleanly separated from phenol under these conditions. Mixtures of phenol and N-methyl-2-pyrrolidone in weight ratios of about 50:50 were obtained.

The results of this run show that N-methyl-2-pyrrolidone, a solvent outside the scope of this invention, separates cyclohexanone in high yield and high purity from a mixture of phenol and cyclohexanone and CHB, but cannot be readily recovered for recycle.

EXAMPLE V

In a control run, an extractive distillation of a mixture containing 68 weight percent phenol, 27 weight percent cyclohexanone, and 5 weight percent CHB was conducted with phenyl salicylate as solvent. The conditions were 80 mm Hg pressure, 85°–92° C. head temperature, and a 3.06/1 solvent/feed ratio. Over a three-hour run time, the overhead product contained 58.3 weight percent of the cyclohexanone fed to the column with a purity of 33.9 weight percent.

This extractive distillation was repeated with the same solvent, but with the pressure increased to 100 mm Hg, the head temperature increased to 99°–102° C., and the solvent/feed ratio increased to 3.2/1. Over a 4-hour run time, the overhead product contained 90.6 weight percent of the cyclohexanone fed to the columm with a purity of 25.9 weight percent.

Thus, phenyl salicylate, a solvent outside the scope of this invention, does not cleanly separate cyclohexanone from the mixture of cyclohexanone, phenol, and CHB.

EXAMPLE VI

In another control run, an extractive distillation of a mixture containing 70 weight percent phenol and 30 weight percent cyclohexanone was conducted with methyl oleate as solvent. The conditions were 100 mm Hg pressure, 53°–73° C. head temperature, and a solvent/feed volume ratio of 4.2/1. Over a 7-hour run time, the overhead fractions contained 48.1 weight percent of the cyclohexanone fed to the column with a purity of 94.7 weight percent.

Thus, methyl oleate, a solvent outside the scope of this invention, does not cleanly remove cyclohexanone from a mixture of phenol and cyclohexanone.

A run included in the file of this case but not included as an example is the attempted extractive distillation of a phenol-cyclohexanone-CHB mixture with N-phenyl-2-pyrrolidone, a compound within the scope of this invention. The high melting point (70° C.) of this compound prevented use in the laboratory equipment due to lack of suitable heating equipment for the solvent introduction system. However, it is believed that with proper equipment a suitable extractive distillation with N-phenyl-2-pyrrolidone would be possible.

Reasonable variation and modification are possible within the scope of the foregoing disclosure, the drawing, and the appended claims to the invention the essence of which is that N-substituted lactam as herein described has been found highly effective for recovery of cyclohexanone by extractive distillation of it from mixtures containing it, phenol, and cyclohexylbenzene.

I claim:

1. An extractive distillation of a mixture containing phenol and cyclohexanone, which mixture may contain cyclohexylbenzene, which comprises distilling said mixture in the presence of a solvent comprising at least one N-substituted lactam.

2. A process according to claim 1 wherein the solvent used in the extractive distillation of this invention contains up to 30 carbon atoms and is represented by the general formula:

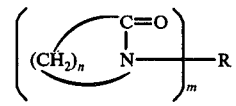

wherein R is selected from a group consisting of alkyl radicals containing 2 to 20 carbon atoms, cycloalkyl radicals containing 5 to 20 carbon atoms, alkylene radicals containing 2 to 20 carbon atoms, aryl or substituted aryl radicals containing 6 to 18 carbon atoms with the substituent groups being one or more or a mixture of alkyl, alkoxy, cycloalkyl, halogen, or the like, arylene radicals containing 6 to 18 carbon atoms, aralkyl radicals containing 7 to 18 carbons and wherein $n$ is an integer from 3 to 8 and $m$ is 1 or 2 and wherein the selected solvent has a boiling point above the boiling point of phenol (182° C. at atmospheric pressure) to facilitate the separation of the solvent for recycling by fractional distillation.

3. A process according to claim 2 wherein the solvent is at least one selected from the following: N-ethyl-2-pyrrolidone, N-butyl-2-pyrrolidone, N-hexadecyl-2-pyrrolidone, N-cyclohexyl-2-pyrrolidone, N-phenyl-2-pyrrolidone, N-(p-methoxyphenyl)-2-pyrrolidone, N-benzyl-2-pyrrolidone, p-phenylene-N,N'-bis(2-pyrrolidone),hexamethylene-N,N'-bis(2-pyrrolidone), and N-ethyl-2-piperidone.

4. A process according to claim 1 wherein there is recovered as an overhead product substantially pure cyclohexanone and a bottoms product containing phenol, cyclohexylbenzene when it has been present, and the N-substituted lactam solvent and wherein the solvent is recovered and reused.

* * * * *